(12) United States Patent
Tung et al.

(10) Patent No.: US 6,844,475 B1
(45) Date of Patent: Jan. 18, 2005

(54) LOW TEMPERATURE PRODUCTION OF 1-CHLORO-3,3,3-TRIFLUOROPROPENE (HCFC-1233ZD)

(75) Inventors: Hseuh Sung Tung, Getzville, NY (US); Kevin D. Ulrich, Alden, NY (US); Daniel C. Merkel, West Seneca, NY (US)

(73) Assignee: Honeywell International Business Machines, Morristown, NJ (US)

( * ) Notice: Subject to any disclaimer, the term of this patent is extended or adjusted under 35 U.S.C. 154(b) by 0 days.

(21) Appl. No.: 10/637,976

(22) Filed: Aug. 8, 2003

(51) Int. Cl.[7] .................... C07C 17/04; C07C 17/013; C07C 17/087; C07C 17/07; C07C 17/00
(52) U.S. Cl. .................. 570/168; 570/164; 570/165; 570/166; 570/169
(58) Field of Search ................................ 570/168, 164, 570/165, 166, 169

(56) References Cited

U.S. PATENT DOCUMENTS

| | | | |
|---|---|---|---|
| 5,710,352 A | 1/1998 | Tung ........................ | 570/166 |
| 6,018,084 A | 1/2000 | Nakada et al. .............. | 570/166 |
| 6,077,982 A | 6/2000 | Yates et al. ................. | 570/177 |
| 6,111,150 A | 8/2000 | Sakyu et al. ................ | 570/167 |
| 6,198,010 B1 | 3/2001 | Yoshikawa et al. ......... | 570/167 |
| 6,235,951 B1 | 5/2001 | Sakyu et al. ................ | 570/156 |
| 6,316,681 B1 | 11/2001 | Yoshikawa et al. ......... | 570/166 |
| 6,362,383 B1 | 3/2002 | Wilmet et al. .............. | 570/166 |
| 6,403,847 B1 | 6/2002 | Nakada et al. .............. | 570/156 |
| 6,414,203 B1 | 7/2002 | Okamoto et al. ........... | 570/177 |
| 6,472,573 B1 | 10/2002 | Yamamoto et al. ......... | 570/164 |
| 2003/0060669 A1 | 3/2003 | Shibata et al. .............. | 570/136 |

FOREIGN PATENT DOCUMENTS

| | | | | |
|---|---|---|---|---|
| EP | 0 939 071 A1 | 9/1999 | .......... | C07C/19/08 |
| JP | 2002-7592 | 1/2000 | | |
| WO | WO 96/01797 | 1/1996 | .......... | C07C/17/20 |

*Primary Examiner*—Elvis O. Price
(74) *Attorney, Agent, or Firm*—Colleen D. Szuch

(57) ABSTRACT

A process for producing 1-chloro-3,3,3-trifluoropropene (HCFC-1233zd) from 1,1,1-3,3-pentachloropropane (HCC-240fa) by its reaction with hydrogen fluoride, the reactants are reacted in a liquid phase reaction at a temperature of less than 150° C. in the presence of a Lewis acid catalyst or mixture of Lewis acid catalysts, and hydrogen chloride and HCFC-1233zd formed in the reaction are continuously removed and the HCFC-12333zd is isolated.

11 Claims, No Drawings

LOW TEMPERATURE PRODUCTION OF 1-CHLORO-3,3,3-TRIFLUOROPROPENE (HCFC-1233ZD)

FIELD OF THE INVENTION

This invention relates to the production of 1-chloro-3,3,3-trifluoropropene (HCFC-1233zd) in high yields of over 75% and at lower temperatures than normally employed.

BACKGROUND TO THE INVENTION

1-Chloro-3,3,3-trifluoropropene (HCFC-1233zd) is a raw material used for making 1,1,1,3,3-pentafluoropropane (HFC-245fa). However, it also has other uses, such as for example, as a monomer in the preparation of polymeric materials. It can also be used as a raw material as a building block for making other fluorinated compounds. The preparation of HFC-245fa from HCFC-12333zd is a two-step process, such as disclosed in WO 97/24307. In this two-step process 1,1,1-3,3-pentachloropropane (HCC-240fa) first reacts, in the gas phase, with hydrogen fluoride to give 1233zd, which, after the removal of HCl formed, reacts in a second step with hydrogen fluoride to give HFC-245fa. This gaseous phase reaction is generally carried out at temperatures of 180° C. or higher, preferably higher. In another process disclosed in U.S. Pat. No. 6,362,383, it is taught that the production of HFC-245fa at about 120° C. can be improved by first reacting HCC-240fa with hydrogen fluoride in liquid phase in the presence of a hydrofluorination catalyst to produce HCFC-1233zd and other reaction products, and in a second step the HCFC-1233zd obtained from the first step is reacted with hydrogen fluoride in liquid phase in the presence of a second hydrofluorination catalyst to obtain the HFC-245fa, wherein in at least one or both of the steps there is the continuous introduction of hydrogen chloride into the reaction medium. In Example 1 of this patent, the first step of the reaction, with the introduction of hydrogen chloride, produces HCFC-1233zd as only 3.3% of the reaction products after 2.5 hours and 1.55% of the reaction products after 22 hours. In the second Example in this patent, when HCl is not continuously fed into the reaction medium, the production of HCFC-1233zd in the first step after 2.5 hours is 64.6% and after 22 hours is 11.9% of the reaction products. This prior art teaches introduction of hydrogen chloride to the reaction mixture to minimize formation of HCFC-1233zd.

In view of the other substantial markets for HCFC-1233zd there is a need for the ability to produce HCFC-1233zd in as high a yield as possible, and in greater yields than shown to be possible in U.S. Pat. No. 6,362,383. Moreover, it is also desirable to be able to produce HCFC-1233zd in high yield in a process that is able to utilize low reaction temperatures of 150° C. or less, preferably less, so that high pressure and the need for expensive equipment can be avoided. Moreover, it is highly desirable that such a process be available that produces HCFC-1233zd in increased higher yields so that large amounts of by-products can be avoided.

SUMMARY OF THE INVENTION

This invention provides a process, batch or continuous, for the production of HCFC-1233zd from HCC-240fa in high yields, i.e., in yields of reaction products of higher than about 75%, preferably higher than about 80%, and even more preferably higher than about 90%, and by a process that can be conducted at a temperature of 150° C. or less and in the liquid phase. Yields of greater than about 75%, preferably greater than a bout 80%, and more preferably greater than about 90%, of HCFC-1233zd from the reaction of HCC-240fa with anhydrous hydrogen fluoride can be obtained if the reactants are reacted at a temperature of less than 150° C. in the presence of a Lewis acid catalyst or mixture of Lewis acid catalysts, provided that hydrogen chloride and HCFC-1233zd formed in the reaction are continuously removed after their formation, and the HCFC-1233zd isolated.

DETAILED DESCRIPTION OF THE INVENTION AND PREFERRED EMBODIMENTS

In accordance with this invention, HCFC-1233zd is produced in yields of greater than about 75% of the reaction products when HCC-240fa is reacted with substantially anhydrous hydrogen fluoride in a liquid phase reaction, if the reactants are reacted at a temperature of less than 150° C. in the presence of a Lewis acid catalyst or mixture of Lewis acid catalysts, provided that hydrogen chloride and HCFC-1233zd formed in the reaction are continuously removed after their formation. Such a liquid phase reaction at 150° C. or less can produce reaction products wherein HCFC-1233zd comprises at least about 75%, preferably at least about 80% and more preferably about 90% of the reaction products produced by the reaction.

The liquid phase reaction of HCC-240fa with substantially anhydrous hydrogen fluoride to produce the high proportion of HCFC-1233zd reaction product can be conducted at a temperature of 150° C. or less, preferably at a temperature of about 40° to about 130° C., and more preferably at a temperature of from about 50° to about 120° C.

The reaction can generally be conducted at a pressure of from about 50 to about 600 psig (about 3.515 to about 42.18 kg/cm$^2$), preferably from about 80 to about 500 psig (about 5.62 to about 35.15 kg/cm$^2$), more preferably at a pressure of about 100 to about 400 psig (about 7.03 to about 28.12 kg/cm$^2$), and even more preferably at about or no more than about 200 psig (about 14.06 kg/cm$^2$).

The mole ratio of HCC-240fa to hydrogen fluoride reactant will generally be from about 3:1 to about 30:1, preferably from about 4:1 to about 25:1 and more preferably from about 5:1 to about 20:1. The molar rations are expressed, in the case of a batch process, relative to the initial amounts used, and, in the case of a continuous process, relative to the stationery amounts in the reaction medium.

The catalyst employed in the reaction is a Lewis acid catalyst or mixture of Lewis acids. Any suitable Lewis acid catalyst or mixture thereof may be employed as the catalyst for the reaction. Such suitable Lewis acid catalysts include, but are not limited to, transition metal halides and Group IIIb, IVb and Vb metal halides. Preferred are titanium, tin and iron halides and mixtures thereof, especially titanium tetrachloride, tin tetrachloride and iron chloride and mixtures thereof. As examples of other suitable Lewis acid catalysts there may be mentioned, for example, $SbCl_5$, $SbCl_3$, $TaCl_5$, $NbCl_5$, $MoCl_5$ and the like. Any suitable catalytic amount of Lewis acid catalyst or mixture may be employed in the reaction.

By "substantially anhydrous hydrogen fluoride" it is meant that the hydrogen fluoride generally contains less than about 0.05 weight % water, and more preferably contains less than about 0.02 weight % water since water will react with and deactivate the reaction catalyst. Substantially anhydrous hydrogen fluoride suitable for use in the reaction may be obtained from Honeywell or Air Products.

The reaction may be conducted as either a batch reaction or a continuous reaction and with or without a solvent. In either case, the HCFC-1233zd and hydrogen chloride formed are continuously removed from the batch or continuous reaction mixture by any suitable removal means. A useful solvent is an organic compound that dissolves the starting material HCC-240fa and that has a boiling point higher than that of the product, HCFC-1233zd. In addition, such a solvent would not be fluorinated by HF in any substantial amount during the course of the reaction. Examples of useful solvents include, but are not limited to, sulfolane, perfluorinated alkanes and alkenes, hydrofluorocarbons (HFCs) and hydrofluorocarbons (HCFCs). The amount of solvent employed will generally be from about 10% to about 80%, preferably from about 20% to about 60%, based on the total weight of the reaction mixture.

The HCFC-1233zd and HCl are generally removed as soon as they are formed in the reaction mixture and can be removed by any suitable means, such as for example, by means of a distillation column and/or water condensed cooler fitted to an outlet, such as a pressure control valve, on the reaction vessel. Upon removal of the HCFC-1233zd from the reaction mixture, HCFC-1233zd is isolated and removed from any under-reacted intermediates in the vapor phase and the under-reacted intermediates of the vapor phase are recycled back to the reaction vessel where they are further reacted with HF to produce additional HCFC-1233zd.

The invention is illustrated by, but not limited to, the following examples.

EXAMPLE 1

To an empty 4 L reactor at room temperature, 90 g of TiCl$_4$, 746 g of anhydrous HF and 1437 g of 1,1,1,3,3-pentachloropropane were charged. A water-cooled condenser is fitted to the outlet of the reactor with provision to return any condensed unreacted HF and unreacted 240fa and intermediates back to the reactor. A pressure control valve is fitted to the vapor outlet of the condenser. The reactor system was sealed and the temperature gradually increased to 120° C. with agitation over 70 minutes. The reaction products of 1233zd and HCl were continuously removed through a pressure control valve to maintain a maximum of 360 psig and were scrubbed through a dilute KOH/water solution and collected. GC Analysis of the scrubbed vapors gave 82 area % 1-chloro-3,3,3-trifluoropropene and 18% of HFC-245fa and under-reacted intermediates. Recycle of the under-reacted intermediates in the vapor phase as well as those left in the reactor bring the overall yield of HCFC-1233zd to greater than 90%.

EXAMPLE 2

To an empty 38-liter reactor vessel fitted with a distillation column, water-cooled condenser and pressure control valve, 23.6 kg (109 g mole) of 1,1,1,3,3-pentachloropropane, 1.2 kg of TiCl$_4$, and 18.2 kg of anhydrous HF were charged. The reactor was heated to 90° C. with agitation while the cooling water flow to the condenser and the pressure control valve was adjusted to preferentially remove 1-chloro-3,3,3-trifluoropropene and HCl from the system. The reactor pressure was controlled at 200 psig. Product was continuously taken off the reactor and scrubbed through a 30° C. 10% KOH solution and then collected in a cold trap. A total of 10.1 kg of product was collected consisting of 79.7 wt % 1-chloro-3,3,3-trifluoropropene.

EXAMPLE 3

To the reactor system described in example 2, the reactor vessel is charged with 1.2 kg of TiCl$_4$ and 0.76 kg of HF. The reactor is brought up to 90° C. and 200 psig. Then 1 kg/hr of 1,1,1,3,3-pentachloropropane and 0.3 kg/hr of HF are continuously fed to the reactor. The condenser cooling water is adjusted to maintain constant level in the reactor. Products of 1233zd and HCl are continuously taken off the reactor and scrubbed through a 30° C. 10% KOH solution and then collected. Collected material consists of 85 wt % 1-chloro-3,3,3-trifluoropropene. The 15% balance of the collected material contains under-reacted intermediate, and this balance of material is recycled to the reaction vessel for reprocessing and this increases the overall yield of HCFC-1233zd to 90%.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

We claim:

1. A process for producing 1-chloro-3,3,3-trifluoropropene (HCFC-1233zd) from the reactants 1,1,1-3,3-pentachloropropane (HCC-240fa) and anhydrous hydrogen fluoride, the process comprising reacting the reactants in a liquid phase reaction in a reaction vessel at a temperature of less than 150° C. in the presence of a Lewis acid catalyst or mixture of Lewis acid catalysts, and continuously removing hydrogen chloride and HCFC-1233zd formed in the reaction vessel and isolating the HCFC-12332zd, wherein the HCFC-1233zd produced by the reaction comprises at least more than about 75% of products produced by the reaction.

2. A process according to claim 1 wherein the HCFC-1233zd produced by the reaction comprises at least more than about 80% of products produced by the reaction.

3. A process according to claim 1 wherein the HCFC-1233zd produced by the reaction comprises at least more than about 90% of products produced by the reaction.

4. A process according to claim 1 wherein under-reacted intermediate removed from the reaction vessel with the HCFC-1233zd is recycled back to the reaction vessel and further reacted to produce additional HCFC-1233zd.

5. A process according to claim 1 wherein the catalyst is selected from the group consisting of a transition metal halides and Group IIIb, IVb and Vb metal halides and mixtures thereof.

6. A process according to claim 1 wherein the catalyst is selected from the group consisting of titanium tetrachloride, tin tetrachloride, iron chloride and mixtures thereof.

7. A process according to claim 5 wherein the catalyst is titanium tetrachloride.

8. A process according to claim 1 wherein the reaction is conducted at a temperature of about 90° C.

9. A process according to claim 8 wherein the catalyst is titanium tetrachloride and the reaction is conducted as a continuous reaction.

10. A process according to claim 9 wherein the reaction is conducted at a pressure of no more than 200 psig (14.06 kg/cm$^2$).

11. A process according to claim 9 wherein under-reacted intermediate removed from the reaction vessel with the HCFC-1233zd is recycled back to the reaction vessel and further reacted to produce additional HCFC-1233zd.

* * * * *

UNITED STATES PATENT AND TRADEMARK OFFICE
CERTIFICATE OF CORRECTION

| | | |
|---|---|---|
| PATENT NO. | : 6,844,475 B1 | Page 1 of 1 |
| APPLICATION NO. | : 10/637976 | |
| DATED | : January 18, 2005 | |
| INVENTOR(S) | : Hseuh Sung Tung, Kevin D. Uhrich and Daniel C. Merkel | |

It is certified that error appears in the above-identified patent and that said Letters Patent is hereby corrected as shown below:

Inventor [75]: Delete "Kevin D. Ulrich" replace with --Kevin D. Uhrich--

Assignee [73]: Delete "Honeywell International Business Machines" replace with --Honeywell International Inc.--

Column 1, line 19, delete "HCFC-12333zd" and replace with --HCFC-1233zd--

Column 4, line 30, delete "HCFC-12332zd" and replace with --HCFC-1233zd--

Signed and Sealed this

Sixteenth Day of January, 2007

JON W. DUDAS
*Director of the United States Patent and Trademark Office*